US005836865A

United States Patent [19]

Ritchie et al.

[11] Patent Number: 5,836,865

[45] Date of Patent: Nov. 17, 1998

[54] MALE SEX AID

[76] Inventors: Steven D. Ritchie, 368 Bay Plz., Treasure Island, Fla. 33706; Harley David Reynard, 5054 Johns Pass Ave., Madera Beach, Fla. 33708

[21] Appl. No.: 949,935

[22] Filed: Oct. 14, 1997

[51] Int. Cl.[6] ........................ A61F 5/00

[52] U.S. Cl. ........................ 600/38; 600/39; 600/41; 607/108

[58] Field of Search ........................ 600/38, 39, 41; 601/6, 7, 11, 33, 34, 35, 40, 39; 607/108, 109, 110, 111

[56] References Cited

U.S. PATENT DOCUMENTS 4,407,275 10/1983 Schroeder ........................ 600/38

5,411,541 5/1995 Bell et al. ........................ 607/104

*Primary Examiner*—John P. Lacyk

*Assistant Examiner*—Rosiland Kearney

[57] ABSTRACT

A male sex aid device is disclosed. Such device includes a first sheet of a flexible material having a length and a width and a thickness to thereby form side edges and end edges. A second sheet of a flexible material having a length and a width and a thickness to thereby form side edges and end edges is also provided. The sheet material is shaped and coupled to form a tube of a plurality of inflatable pillows of similar configuration. A filler valve is formed in the exterior surface of each pillow whereby when the plurality of pillows are inflated through the filler valve, there will be formed a small opening along the length of the tube for the receipt of a penis.

4 Claims, 3 Drawing Sheets

FIG 3
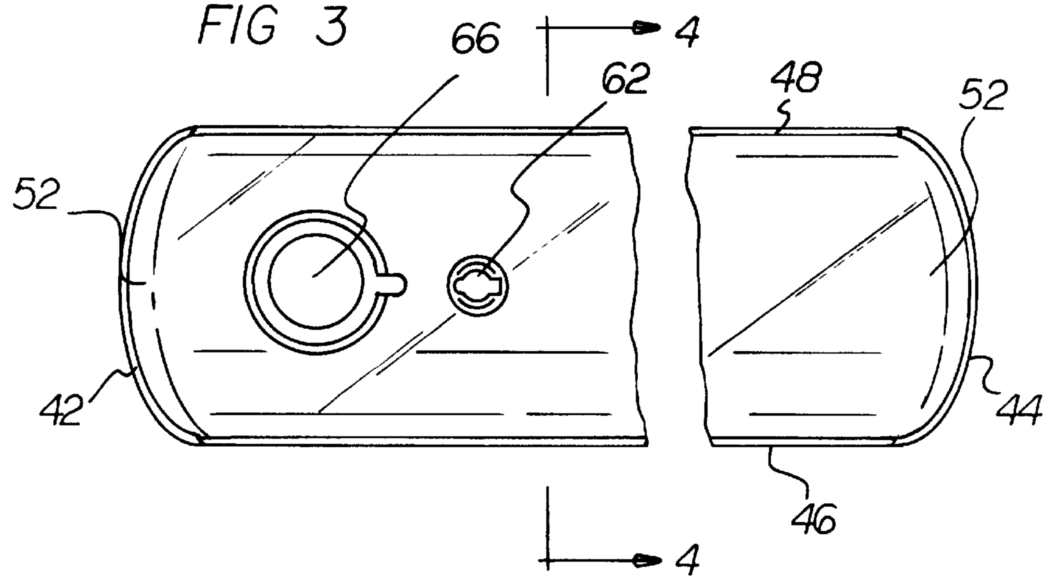
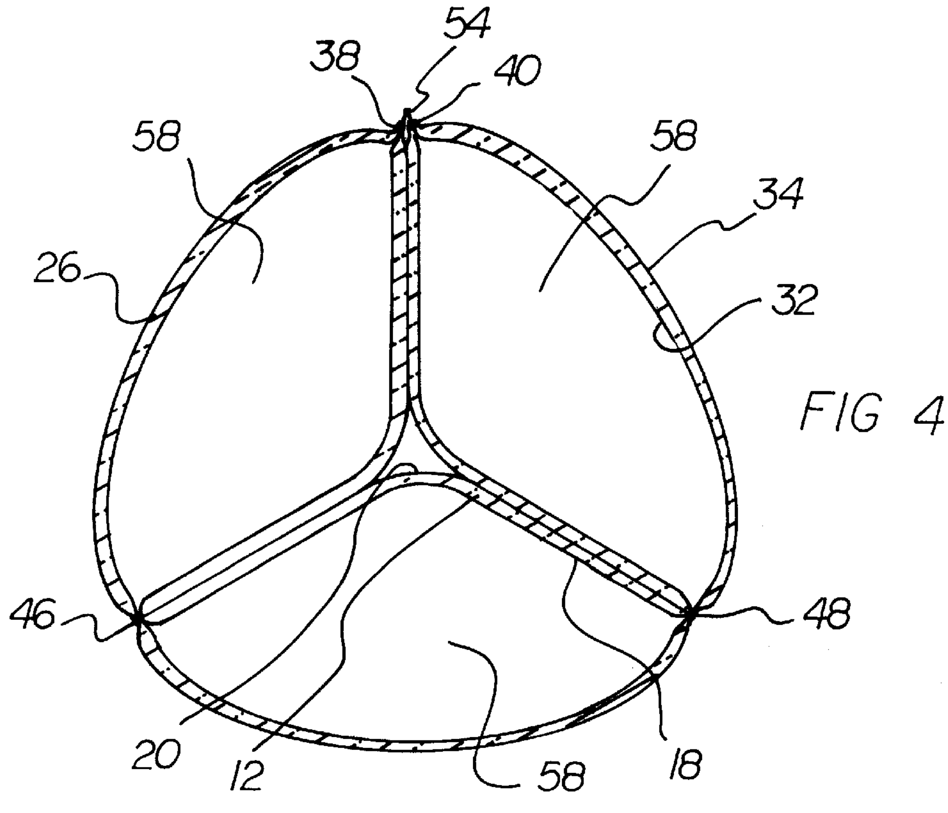
FIG 4

FIG 5
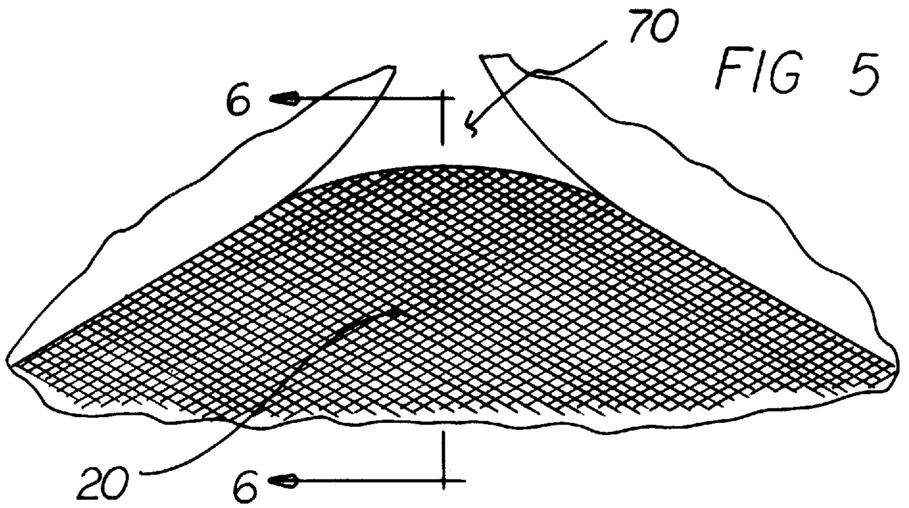
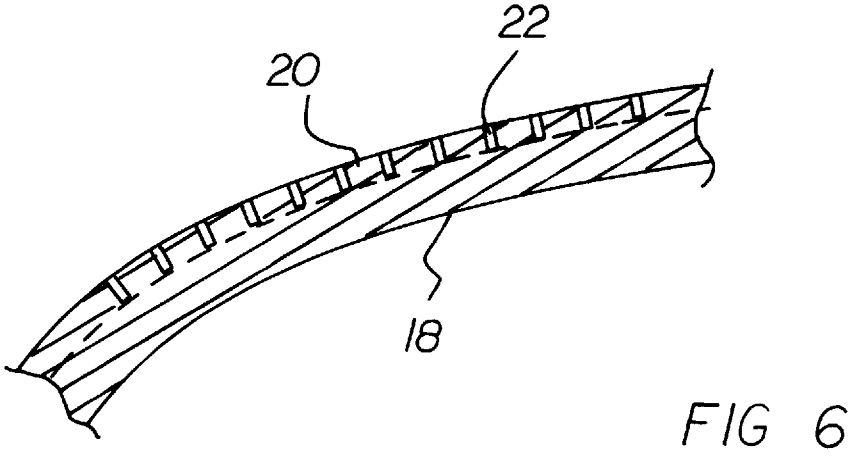
FIG 6

MALE SEX AID

BACKGROUND OF THE INVENTION

1. Field of the Invention

The present invention relates to a new and improved male sex aid and, more particularly, pertains to sexually stimulating a penis.

2. Description of the Prior Art

The use of sex aids of various designs and configurations is known in the prior art. More specifically, sex aids of various designs and configurations heretofore devised and utilized for the purpose of stimulating sex organs through various methods and apparatuses are known to consist basically of familiar, expected, and obvious structural configurations, notwithstanding the myriad of designs encompassed by the crowded prior art which has been developed for the fulfillment of countless objectives and requirements.

The prior art discloses a large number of sex aids of various designs and configurations. By way of example, U.S. Pat. No. 4,607,402; U.S. Pat. No. 4,300,542 and U.S. Pat. No. 4,72,327 are cited as being of general interest.

In this respect, the male sex aid according to the present invention substantially departs from the conventional concepts and designs of the prior art, and in doing so provides an apparatus primarily developed for the purpose of sexually stimulating a penis.

Therefore, it can be appreciated that there exists a continuing need for a new and improved male sex aid which can be used for sexually stimulating a penis. In this regard, the present invention substantially fulfills this need.

SUMMARY OF THE INVENTION

In view of the foregoing disadvantages inherent in the known types of sex aids of various designs and configurations now present in the prior art, the present invention provides a new and improved male sex aid. As such, the general purpose of the present invention, which will be described subsequently in greater detail, is to provide a new and improved male sex aid and methods which have all the advantages of the prior art and none of the disadvantages.

To attain this, the present invention essentially comprises a new and improved male sex aid device for the sexual stimulation of a penis comprising, in combination, a first sheet of a flexible vinyl material about 24 inches in length and about 15 inches in width and about 0.014 inches in thickness to thereby form long side edges and short end edges, the entire first sheet having a smooth interior surface over its entire extent and a textured exterior surface formed with shallow indentations of about 0.007 inches in depth in a grid-like pattern over its entire extent; a second sheet of a flexible vinyl material about 24 inches in length and about 15 inches in width and about 0.014 inches in thickness to thereby form long side edges and short end edges, the entire second sheet having a smooth interior surface over its entire extent and an exterior surface; the first and second sheets being superimposed, one over the other, with two long heat sealing lines coupling the long side edges of the sheets and two short heat sealing lines coupling the short end edges of the sheets and with two additional long heat sealing lines parallel with the long side edges equally spaced about five inches from the long side edges, and with both short end edges being formed with three convex projections, each convex projection having a radius of about five inches between the four long heat sealing lines, and further including a fifth heat sealing line coupling the long side edges to thereby form a two-ply tube from the heat sealed sheets; three inflatable pillows of similar configuration being formed between the two sheets of the tube radially and between and the five heat sealing lines of the tube circumferentially; a small air filler valve located on the exterior surface of the second sheet adjacent to one short edge of each pillow; a large water filler valve located on the exterior surface of the second sheet between the air filler valve and the adjacent short edge of each pillow; and the two sheets and heat sealing lines being configured whereby when the three pillows are inflated through a valve, there will be formed a small generally triangular opening with a textured surface along the length of the tube for the receipt of a penis.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved male sex aid which has all the advantages of the prior art sex aids of various designs and configurations and none of the disadvantages.

It is another object of the present invention to provide a new and improved male sex aid which may be easily and efficiently manufactured and marketed.

It is a further object of the present invention to provide a new and improved male sex aid which is of a durable and reliable construction.

An even further object of the present invention is to provide a new and improved male sex aid which is susceptible of a low cost of manufacture with regard to both materials and labor, and which accordingly is then susceptible of low prices of sale to the consuming public, thereby making such a male sex aid economically available to the buying public.

Even still another object of the present invention is to sexually stimulate a penis.

Lastly, it is an object of the present invention to provide a male sex aid device. Such device includes a first sheet of a flexible material having a length and a width and a thickness to thereby form side edges and end edges. A second sheet of a flexible material having a length and a width and a thickness to thereby form side edges and end edges is also provided. The sheet material is shaped and coupled to form a tube of a plurality of inflatable pillows of similar configuration. A filler valve is formed in the exterior surface of each pillow whereby when the plurality of pillows are inflated through the filler valve, there will be formed a small opening along the length of the tube for the receipt of a penis.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an elevational view of one of the three pillows taken along line 3—3 of FIG. 2.

FIG. 4 is a cross-sectional view taken along line 4—4 of FIG. 3.

FIG. 5 is an enlarged front elevational view of the opening formed by the inflated pillows taken at circle 5 of FIG. 2.

FIG. 6 is a cross-sectional view taken along line 6—6 of FIG. 5.

The same reference numerals refer to the same parts throughout the various Figures.

DESCRIPTION OF THE PREFERRED EMBODIMENT

Figure 1:
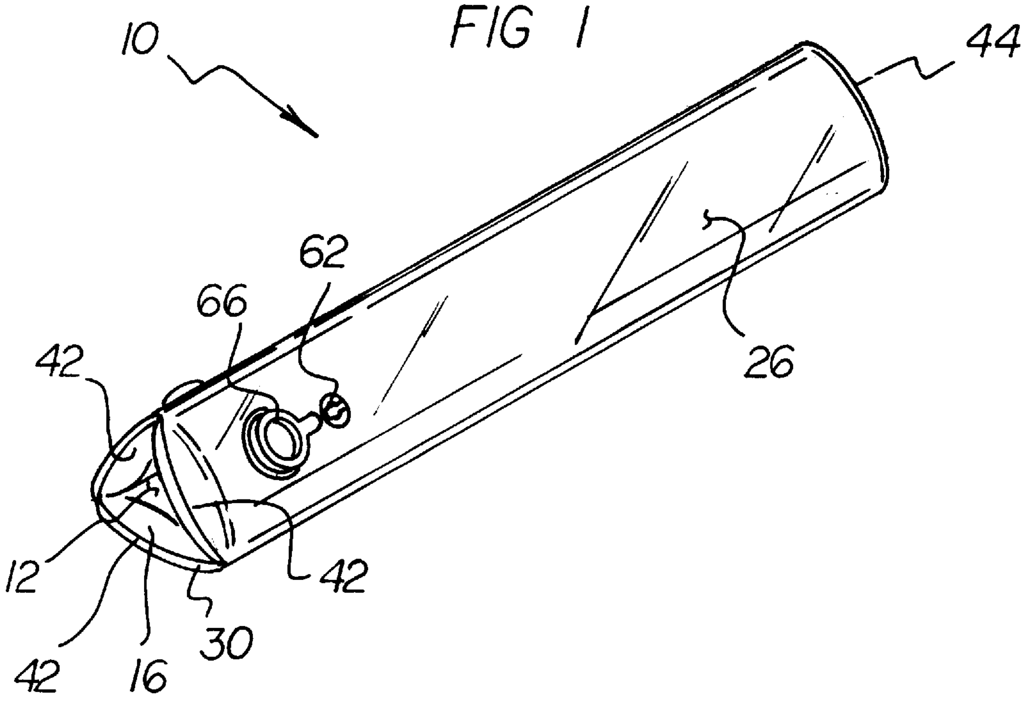
FIG. 1 is a perspective illustration of the new and improved male sex aid constructed in accordance with the principles of the present invention.

With reference now to the drawings, and in particular to FIGS. 1 through 6 thereof, the preferred embodiment of the new and improved male sex aid embodying the principles and concepts of the present invention and generally designated by the reference numeral 10 will be described.

The present invention, the new and improved male sex aid is a device 10 comprised of a plurality of components. Such components, in their broadest context, include a first sheet, a second sheet, heat sealing lines, formed pillows and air and water filler valves. Each of the individual components is specifically configured and correlated one with respect to the other so as to attain the desired objectives.

Specifically, the device 10 of the present invention includes as a primary component a first sheet 12 of a flexible plastic material, impervious to air and water, preferably vinyl. The first sheet is about 24 inches in length and about 15 inches in width. It has a thickness of about 0.014 inches. In this manner, the device forms long side edges 14 and short end edges 16. The entire sheet has a smooth interior surface 18 over its entire extent. The sheet is preferably fabricated to include a textured exterior surface 20. The textured exterior surface is formed with shallow indentations 22. The indentations are formed of about 0.007 inches in depth. They are preferably linear in a grid-like pattern over the entire extent of the exterior surface to provide greater sensation to the user during operation and use.

Next provided as a primary component of the device 10 of the present invention is a second sheet 26. The second sheet is of a construction similar to the first sheet 12. It is preferably fabricated of a flexible vinyl material, impervious to air and water. It, too, is about 24 inches in length and about 15 inches in width with a thickness of about 0.014 inches. In this manner, the second sheet also forms long side edges 28 and short end edges 30. The entire second sheet preferably is formed with a smooth interior surface 32 over its entire extent and also includes an exterior surface 34.

The fabrication of the sheets to form the device includes a composite with the first and second sheets being superimposed, one over the other. In such orientation, two long heat sealing lines 38,40 are utilized to couple the long side edges of the sheets. Two short heat sealing lines 42,44 couple the short end edges of the sheets. In addition, there are also provided two additional long heat sealing lines 46,48. Such additional heat sealing lines are parallel with the long side edges. They are spaced equally at about five inches from the long side edges.

In the preferred embodiment, both short end edges are formed with convex projections 52. Each convex projection has a radius of about five inches. Each projection is located between the four heat sealing lines coupling the two sheets together. The last and fifth heat sealing line 54 couples the long side edges. In this manner, there is formed a two-ply tube from the heat sealing sheets.

The orientation of the sheets and heat sealing lines as described above form three inflatable pillows 58. The inflatable pillows are of similar configurations. They are formed between the two sheets of the tube radially and between the five heat sealing lines of the tube circumferentially. In the preferred embodiment, each of the three pillows is independently inflatable.

Next provided as a component of the device is a small air filler valve 62. Such valve is located on the exterior surface of the second sheet. It is positioned adjacent to one short edge of each pillow. The air filler valve is of a conventional design and includes an opening through the second sheet and has a pivotable stopper to preclude passage of air to and from the pillow when closed and to allow the addition of air when opened.

Also provided is a large water filler valve 66. The water filler valve is located on the exterior surface of the second sheet between the air filler valve and the adjacent short edge of each pillow. Each large water filler valve provides an opening through the second sheet for adding water to, or taking water from, its associated pillow. The large water filler valve is of a conventional design. Preferably, the valve has a pivotable stopper adapted to be fitted in the opening to preclude the passage of water to and from the pillow. The stopper is positioned exterior out of the opening to preclude such passage of water. However, the large water filler valve may be of a screw-type plug or the like.

Figure 2:
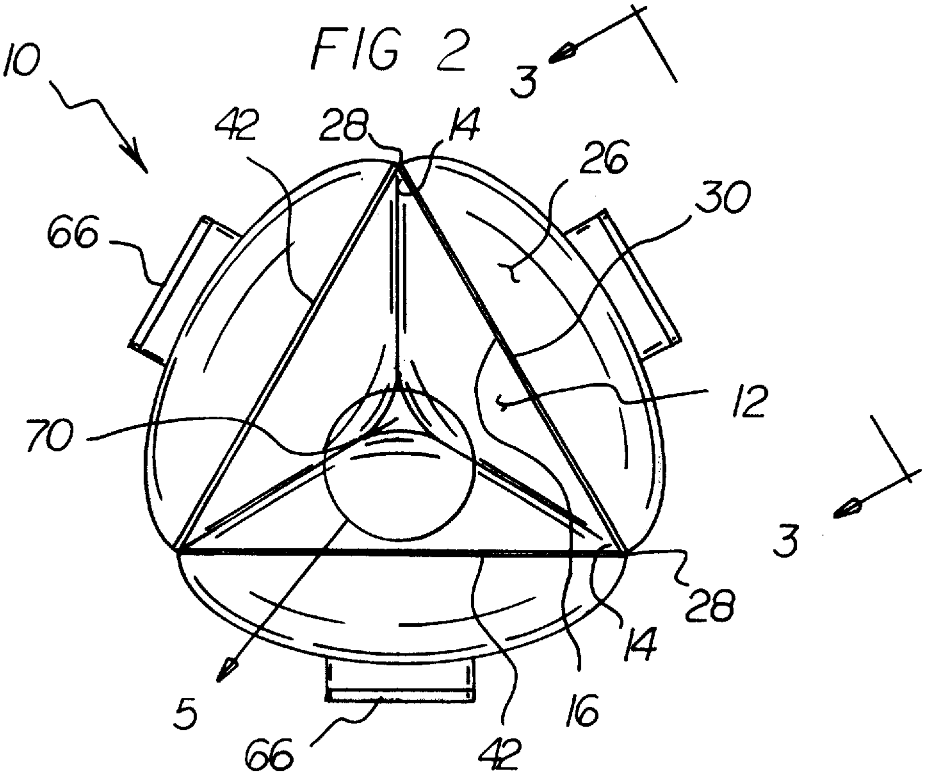
FIG. 2 is a front elevational view of the device shown in FIG. 1.

As can be readily seen by comparing FIGS. 1, 2 and 5, the two sheets and heat sealing lines are configured in such manner whereby when the three pillows are inflated, either through air or water through an appropriate valve, there will be formed a generally triangular opening 70 of a small configuration. The opening is bordered with the textured surface on the exterior side of the first sheet. The triangular opening extends the entire length of the tube and is adapted for the receipt of a penis for the purpose of stimulation.

In operation and use, the device of the present invention should always be used with a lubricant on the penis. As can be understood from the foregoing, the unit may be filled with air or water, individually, or in any combination thereof. Selection of the temperature of the water and/or the air should be selected with care. In addition, during operation and use, the device should be braced with pillows for best result. When not in use, the three pillows should be deflated and emptied for sanitation purposes. Further, for sanitation purposes, the device should be thoroughly washed with mild soap and water after each and every use.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved male sex aid device for the sexual stimulation of a penis comprising, in combination:

a first sheet of a flexible vinyl material about 24 inches in length and about 15 inches in width and about 0.014 inches in thickness to thereby form long side edges and short end edges, the entire first sheet having a smooth interior surface over its entire extent and a textured exterior surface formed with shallow indentations of about 0.007 inches in depth in a grid-like pattern over its entire extent;

a second sheet of a flexible vinyl material about 24 inches in length and about 15 inches in width and about 0.014 inches in thickness to thereby form long side edges and short end edges, the entire second sheet having a smooth interior surface over its entire extent and an exterior surface;

the first and second sheets being superimposed, one over the other, with two long heat sealing lines coupling the long side edges of the sheets and two short heat sealing lines coupling the short end edges of the sheets and with two additional long heat sealing lines parallel with the long side edges equally spaced about five inches from the long side edges, and with both short end edges being formed with three convex projections, each convex projection having a radius of about five inches between the four long heat sealing lines, and further including a fifth heat sealing line coupling the long side edges to thereby form a two-ply tube from the heat sealed sheets;

three inflatable pillows of similar configuration being formed between the two sheets of the tube radially and between and the five heat sealing lines of the tube circumferentially;

a small air filler valve located on the exterior surface of the second sheet adjacent to one short edge of each pillow;

a large water filler valve located on the exterior surface of the second sheet between the air filler valve and the adjacent short edge of each pillow; and the two sheets and heat sealing lines being configured whereby when the three pillows are inflated through a valve, there will be formed a small generally triangular opening with a textured surface along the length of the tube for the receipt of a penis.

2. A new and improved male sex aid device for the sexual stimulation of a penis comprising, in combination:

a first sheet of a flexible vinyl material having a length and a width and a thickness to thereby form long side edges and short end edges, the entire first sheet having a smooth interior surface over its entire extent and a textured exterior surface formed with shallow indentations in a grid-like pattern over its entire extent;

a second sheet of a flexible vinyl material having a length and a width and a thickness to thereby form long side edges and short end edges corresponding with the edges of the first sheet, the entire second sheet having a smooth interior surface over its entire extent and an exterior surface;

the first and second sheets being superimposed, one over the other, with two long heat sealing lines coupling the long side edges of the sheets and two short heat sealing lines coupling the short end edges of the sheets and with two additional long heat sealing lines parallel with the long side edges equally spaced from the long side edges, and with both short end edges being formed with three convex projections, each convex projection having a radius between the four long heat sealing lines, and further including a fifth heat sealing line coupling the long side edges to thereby form a two-ply tube from the heat sealed sheets;

three inflatable pillows of similar configuration being formed between the two sheets of the tube radially and between the five heat sealing lines of the tube circumferentially; and the two sheets and heat sealing lines being configured whereby when the three pillows are inflated, there will be formed a small generally triangular opening with a textured surface along the length of the tube for the receipt of a penis.

3. The new and improved male sex aid device for the sexual stimulation of a penis of claim 2 and further including:

a small air filler valve located on the exterior surface of the second sheet adjacent to one short edge of each pillow.

4. The new and improved male sex aid device for the sexual stimulation of a penis of claim 3 and further including:

a large water filler valve located on the exterior surface of the second sheet between the air filler valve and the adjacent short edge of each pillow.

* * * * *